United States Patent [19]

Papavassiliou et al.

[11] Patent Number: 6,040,467
[45] Date of Patent: Mar. 21, 2000

[54] HIGH PURITY OXYGEN FOR ETHYLENE OXIDE PRODUCTION

[75] Inventors: Vasilis Papavassiliou, Kent; Matthew Lincoln Wagner, White Plains, both of N.Y.; Roger William Day, Southbury, Conn.

[73] Assignee: Praxair Technology, Inc., Danbury, Conn.

[21] Appl. No.: 08/899,706

[22] Filed: Jul. 24, 1997

[51] Int. Cl.[7] .......................... C07D 301/10; C07D 301/03
[52] U.S. Cl. ............................................ 549/534; 549/535
[58] Field of Search ...................................... 549/534, 535

[56] References Cited

U.S. PATENT DOCUMENTS

| | | | |
|---|---|---|---|
| 3,083,213 | 3/1963 | Courter | 260/348.5 |
| 3,119,837 | 1/1964 | Kingsley et al. | 260/348.5 |
| 3,664,970 | 5/1972 | De Maid | 252/454 |
| 4,769,047 | 9/1988 | Dye | 55/26 |
| 4,879,396 | 11/1989 | Ozero | 549/534 |
| 4,904,807 | 2/1990 | Ozero | 549/534 |
| 5,262,551 | 11/1993 | Horrell, Jr. et al. | 549/534 |

OTHER PUBLICATIONS

"An Experimental Study of the Kinetics of the Selective Oxidation of Ethene Over A Silver On a–Alumina Catalyst" P. Borman, et al., Ind. Eng. Chem Res., 1995, vol. 34, pp. 49–58.

*Primary Examiner*—Amelia Owens
*Attorney, Agent, or Firm*—Bernard Lau

[57] ABSTRACT

This invention is directed to a method for producing ethylene oxide comprising feeding ethylene, high purity oxygen and a ballast gas with a recycle gas in a catalyst filled reactor to form a gaseous mixture; passing the gaseous mixture from the reactor to a recovery unit to selectively separate ethylene oxide and carbon dioxide containing gas; passing at least a portion of the carbon dioxide containing gas to a stripping unit to selectively separate carbon dioxide and a waste gas; passing at least a portion of the waste gas to purge and another portion for recycling as the recycle gas; and recovering ethylene oxide from the recovery unit.

8 Claims, 2 Drawing Sheets

HIGH PURITY OXYGEN FOR ETHYLENE OXIDE PRODUCTION

FIELD OF THE INVENTION

This invention relates to a method for producing ethylene oxide, and more particularly to a method for producing ethylene oxide by selective oxidation of ethylene using high purity oxygen.

BACKGROUND OF THE INVENTION

Ethylene oxide is produced commercially by the silver-catalyzed partial oxidation of ethylene with oxygen. The oxygen source may be commercially available oxygen or air. Generally, in an oxygen-based process, ethylene, oxygen and a ballast gas are mixed with a recycle gas and fed to the reactor. The reactor comprises a number of tubes which are placed inside a vessel and arranged similar to shell and tube heat exchangers. The reactor tubes are filled with a silver catalyst placed on a porous support containing small amounts of promoters. A coolant circulates in the shell around the reactor tubes to maintain temperature control.

In an oxygen-based process, a typical composition of the gas stream fed to the reactor tubes includes 20 to 30 mol % ethylene, 5 to 10 mol % oxygen, 4 to 20 mol % argon, 30 to 50 mol % ballast gas, 1 to 15 mol % carbon dioxide, with ethane, water and a small amount of ethylene dichloride constituting the remainder of the composition. Ethylene reacts with oxygen to form the reaction product ethylene oxide, and byproducts carbon dioxide and water inside the catalyst filled tubes. The reactions are exothermic and hot spots may be formed within the reactor tubes. "Hot spots" are localized areas of high temperature in the reactor. Hot spots may cause an unwanted runaway reactive condition if not properly controlled.

In an oxygen-based process, the ballast gas is introduced into the reactor in order to obtain optimum reaction mixtures, to control temperature and to avoid the presence of flammable mixtures. High temperature favors the undesirable production of carbon dioxide and reduces both catalyst activity and catalyst life. By controlling the reaction rates and the removal of heat from the reaction zone, the temperature and location of the hot spots can be controlled in order to maximize selectivity to ethylene oxide and preserve the catalyst activity. The ballast gas systems disclosed in the past have included methane, ethane, nitrogen, carbon dioxide, and mixtures of these gases. Methane is preferable to nitrogen as a ballast gas because it has better thermal properties. These thermal properties include a higher molar heat capacity and higher thermal conductivity. U.S. Pat. No. 3,119,837 discloses that ethylene oxide yield will increase as methane replaces nitrogen in the ballast gas.

In an oxygen-based process, the reactor effluent is treated in two separate steps: first, remove product ethylene oxide; and second, remove byproduct carbon dioxide. The remaining gas is recycled to the reactor after a portion of it is purged. A significant amount of ethylene is lost to the purge stream as a selectivity loss. Ballast gas is also lost in the purge stream and must be replenished with fresh ballast gas feed. The purge is required in order to keep impurities in the gas mixture entering the reactor at acceptable levels. One impurity, argon, is introduced in the oxygen stream. Other impurities, like ethane or propane, are found in the ethylene feed stream.

Ethylene oxide production may involve an air-based process instead of an oxygen-based process. In the air-based process, unreacted gases may be recycled to the reactor, but the extent of this recycling is limited by the necessity to remove excess nitrogen from the process. Nitrogen is continuously added to the process as air is added to the oxidation reactor. When nitrogen is removed, an appreciable portion of the unreacted ethylene is lost along with the nitrogen. In order to limit the loss of ethylene under these conditions, the withdrawn gases are mixed with additional air and passed through one or more additional oxidation reactors in the presence of the silver catalyst under more extreme reaction conditions. However, the additional oxidation reactor (or reactors) significantly increases the capital cost of the ethylene oxide plant. Another disadvantage of an air-based process is that a lower rate of ethylene conversion is obtained.

Major differences exist between the purging of air-based and oxygen-based processes. The air-based process requires a substantial purge stream and a staged reaction-absorption system. With the oxygen-based stream, there is a significant reduction in the amount of inert gases introduced into the closed cycle as compared to the air-based process, resulting in a substantially smaller purge and an almost complete recycle of the unconverted ethylene. However, the carbon dioxide formed in the reactor must be removed on a continuous basis. Additionally, a process purge is required in order to prevent the accumulation of argon in the recycle gas. Argon is a major impurity in an oxygen supply derived from a cryogenic air separation plant. The oxygen source for ethylene oxide production plants is typically a cryogenic plant.

A typical oxygen purity usage in ethylene oxide production plants using the oxygen-based process is from 95% to 99.5%. Various methods for treating the purge from oxygen-based ethylene oxide production plants to recover ethylene have been proposed. For example, U.S. Pat. No. 4,904,807 discloses the use of an argon selective membrane that is used to treat the purge and separate it into two streams 1) an argon rich stream that is vented and 2) an ethylene rich stream that can be recycled back to the ethylene oxide reactor, and U.S. Pat. No. 4,769,047 discloses the use of pressure swing adsorption to remove ethylene from the purge and recycle it back to the reactor. A major disadvantage of these methods is the large capital cost of the associated equipment.

Other patents have discussed ethylene oxide production. U.S. Pat. No. 3,083,213 discloses that the use of high purity oxygen reduces ethylene oxide yield. U.S. Pat. No. 5,262,551 discloses a process for epoxidation of ethylene, wherein ethylene is reacted with oxygen in a mole ratio of between three to nine, in the presence of a silver metal catalyst and a halide gas inhibitor, at a pressure of about 200 to 300 psig. Ethylene feed contained therein is about 30 to 90 mol % ethylene. The particularly high concentration of ethylene feed has been disclosed to demonstrate improved selectivity.

It is believed that there has not been a commercially practical solution to reduce the impurities associated with the production of ethylene oxide. Therefore, there is a need to provide a new method for producing ethylene oxide which maximizes the selectivity and minimizes ethylene loses to purge, thus improving the yield of the ethylene oxide production process.

OBJECTS OF THE INVENTION

It is therefore an object of the invention to provide a method which improves the yield of the oxygen-based process for ethylene oxide production.

It is another object to provide a method for producing ethylene oxide which maximizes the selectivity and minimizes loses to purge.

It is yet another object to provide a method of increasing the selective production of ethylene oxide by adjusting the concentration of at least one of ethylene, methane, oxygen and carbon dioxide.

SUMMARY OF THE INVENTION

This invention is directed to a method for producing ethylene oxide comprising combining ethylene, high purity oxygen and a ballast gas with a recycle gas to form a gaseous reaction mixture; feeding the reaction mixture to a catalyst filled reactor such that an effluent emerges therefrom; passing at least a portion of the effluent from the reactor to a recovery unit to selectively remove ethylene oxide, thereby forming an ethylene oxide depleted gas stream; passing at least a portion of the ethylene oxide depleted gas stream to a stripping unit to selectively remove carbon dioxide therefrom; passing at least a portion of the carbon dioxide depleted gas stream to purge and the remaining portion to recycle as a recycle gas; and recompressing the recycle gas.

This invention is also directed to a method for enhancing the yield of ethylene oxide by reducing the presence of argon during ethylene oxide production, the method comprises combining ethylene, high purity oxygen and a ballast gas with a recycle gas in a catalyst filled reactor to form a gaseous mixture; feeding the reaction mixture to a catalyst filled reactor such that an effluent emerges therefrom; passing at least a portion of the effluent from the reactor to a recovery unit to selectively remove ethylene oxide, thereby forming an ethylene oxide depleted gas stream; passing at least a portion of the ethylene oxide depleted gas stream to a stripping unit to selectively remove carbon dioxide therefrom; passing at least a portion of the carbon dioxide depleted gas stream to purge and the remaining portion to the recycle gas; recompressing the recycle gas; and adjusting the flow of the purge stream to effectively reduce the concentration of the argon. Further, adjustments to the concentration of at least one of ethylene, high purity oxygen, ballast gas and carbon dioxide.

Reducing the concentration of argon enables the adjustment of the concentrations of the other gases in the recycle so as to improve the heat transport properties of the recycle gas. Enhancing heat transport properties of the recycle gas reduces the effects of the hot spots formed in the reactor, thereby increasing selectivity to ethylene oxide and increasing catalyst life.

The recycled gas with a reduced argon concentration will reduce recycle compressor load so as to reduce the compressor work because of the replacement of the heavier gas (argon) with lighter gases (ethylene, and/or methane, and/or oxygen). Alternatively one can increase production of ethylene oxide by increasing the flow rate of the recycle gas with reduced argon concentration and maintain the same compressor load.

This invention is also directed to a method for the production of ethylene oxide comprising reacting ethylene with a high purity oxygen in a mole ratio of ethylene to high purity oxygen of at least about one, in the presence of a catalyst and inhibitor, wherein the feed gas introduced in the reaction zone comprises 15 to 40 mol % ethylene; 4 to 20 mol % argon; 6 to 10 mol % very high purity oxygen; 15 to 65 mol % ballast gas; and 5 to 15 mol % carbon dioxide.

In this invention, the high purity gas contains at least 95% oxygen, and preferably at least about 99.5% oxygen. For purpose of this invention, oxygen gas of at least 99.5% oxygen purity may also be designated as "very high purity oxygen." The ballast gas comprises methane and nitrogen.

The catalyst filled reactor comprises a reactor tube filled with silver on a porous support.

BRIEF DESCRIPTION OF THE DRAWINGS

Other objects, features and advantages will occur to those skilled in the art from the following description of preferred embodiments and the accompanying drawings, in which.

DETAILED DESCRIPTION OF THE INVENTION

Figure 1:
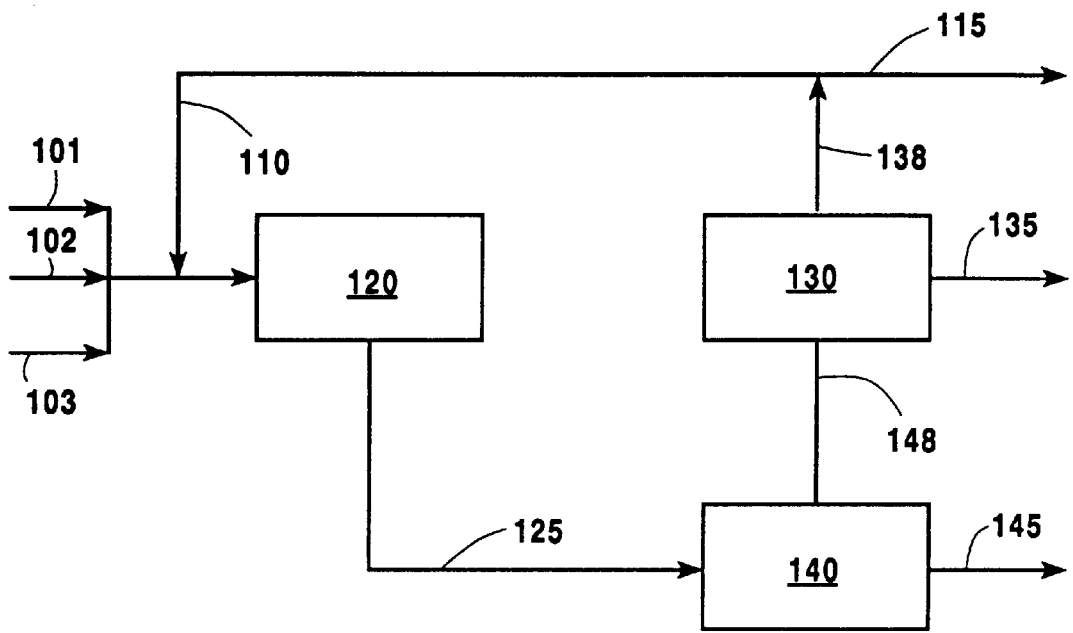
FIG. 1 is a schematic representation of a process for producing ethylene oxide by selective oxidation of ethylene with oxygen.

This invention is directed to an oxygen-based ethylene oxide partial oxidation process that uses a recycle stream. A plant producing 500 MM lb/yr ethylene oxide is used as an example. The gas stream that is fed to the reactor tubes contains about 25 mol % ethylene, 8 mol % oxygen, 16 mol % argon, 42 mol % ballast gas methane, 6.5 mol % carbon dioxide, and the remaining as ethane and water. The selectivity of the reaction is about 80% towards ethylene oxide.

Reducing the purge flow, while keeping the argon concentration in the recycle gas constant, reduces the ethylene loses and ballast gas losses in the purge. Instead of keeping the argon concentration constant and reducing purge flow rate, this invention provides a method for reducing the argon concentration by using high purity oxygen. Reducing the argon concentration enables the increase of ethylene, methane, oxygen or carbon dioxide concentration, or a combination of these four gases to obtain a reactor feed gas composition with better heat transport properties. The reaction rates for the desired ethylene oxide formation and undesired carbon dioxide formation depend on the concentration of all reactant and products. Adjusting the concentrations of reactants and products in the feed can result in an increased yield of ethylene oxide. The purge flow rate will still be smaller than that employed when high purity oxygen is not used.

Thus, there are two reasons for selectivity improvement if the argon concentration decreases: 1) better heat transport properties of the gas fed to the reactor that will reduce the hot spot effect and improve selectivity, and 2) better kinetics through adjusting the remaining gases (reactants and products) concentrations. Improving the selectivity to ethylene oxide means that more of the ethylene that is fed to the reactor is converted to ethylene oxide and less to byproducts. The improvement depends on a variety of conditions including the type and age of the catalyst, and various operating conditions like temperature, pressure and residence time inside the reactor tubes, and the temperature, pressure and flow rate of the coolant fluid flowing in the shell around the reactor tubes.

The selectivity improvement must be determined on a case by case basis because of the differences in the catalyst and the operating conditions used by each commercial plant. It has been reported that if nitrogen is replaced by methane in an ethylene oxide process, the selectivity improves by 0.8 mol % for every 1 mol % reduction of nitrogen. See, U.S. Pat. No. 3,119,837. Increasing the ethylene concentration of the feed from 30.6 mol % to 74.5 mol % will improve the selectivity of from 79.7 mol % to 80.8 mol %. See, U.S. Pat. No. 5,262,551. Replacing argon in the gas feed to the reactor will provide similar benefits.

For the reasons outlined above, when high purity oxygen is used, ethylene selectivity improvement from 0.05 mol % to 1 mol % can be expected for every 1% reduction of the argon concentration if at the same time a combination of the other gases concentrations are increased to replace that of argon. However, reducing the argon concentration will increase the purge flow rate and may also increase the ethylene concentration in the recycle stream, and consequently increase ethylene losses in the purge. Thus, when high purity oxygen is used, there exists an optimum reduced argon concentration in the recycle stream and purge stream flow-rate that will maximize ethylene yield.

Improving the selectivity of the reactor will also allow the increase of ethylene oxide production. If the ethylene feed rate is held constant, and the selectivity improves, additional ethylene oxide is produced. Assuming that the downstream separation equipment is capable of processing the additional load, this constitutes a zero capital method for increasing production in the order of from about 0.5% to about 5.0%.

Reducing the argon concentration also reduces the effects of hot spot formation in the reactor and thus extend the catalyst life. This effect is associated with improving selectivity (which reduces the amount of heat generated within the reactor) and improving the thermal properties of the reaction gas mixture (which improves the heat removal from the reactor). The extension of catalyst life reduces the consumption of the catalyst.

The catalysts employed in the process of this invention may be any silver metal-containing catalysts known in the art for catalyzing the controlled oxidation of ethylene with molecular oxygen to produce ethylene oxide. The catalysts may be a silver metal upon a suitable support. The support may be comprised of a siliceous and aluminous materials. Particularly suitable catalysts are those made of essentially silver metal and promoters on low surface area supports containing alpha alumina along with minor proportions of silica, silicon carbide, and other refractory materials.

In general, the operating temperature of this invention suitably takes place in the range of from about 150° C. to about 350° C., preferably in the range of from about 200° C. to about 300° C., and most preferably in the range of from about 220° C. to about 260° C.

The operating pressure for the practice of this invention is suitably in the range of from about 100 psig to about 400 psig, and preferably from about 200 to 300 psig. The space velocity is chosen according to the desired amount of production, and preferably in the range of from about 3000 to about 4000 hr$^{-1}$. These range of parameters are typically used in the current commercial ethylene oxide production.

The use of high purity oxygen in this invention may also be practiced with a conventional ethylene recovery apparatus for the purge stream, such as membrane separation or pressure swing adsorption, to treat the purge, recover the remaining ethylene and return it to the reactor. The use of high purity oxygen greatly reduces the required capital investment for such systems.

FIG. 1 provides a schematic representation of a process for producing ethylene oxide by selective reduction of ethylene with oxygen. An effective amount of oxygen 101 (which contains argon as impurity), ethylene 102 and ballast gas 103 (nitrogen or methane) are admixed with at least a portion of a recycle gas 110 for feeding into reactor 120. The recycle purge gas 110 and waste purge 115 emerges from a carbon dioxide stripping unit 130. Reactor 120 consists of several tubes inside a shell arranged similar to a heat exchanger. The reactor tubes are filled with a catalyst, which preferably is silver on a porous support like alumina with a small amount of promoters. A reactor effluent stream, 125, containing impure ethylene emerges from the reaction of oxygen (from 101 and 110) and ethylene (from 102 and 110). The reactor effluent 125 is fed into ethylene oxide recovery unit 140. Emerging from the treatment in unit 140 are the ethylene oxide product 145 and carbon dioxide rich stream 148. Carbon dioxide stripping unit 130 converts carbon dioxide rich stream 148 into carbon dioxide 135 and stream 138, which in turn is separated into a recycle 110 for further reaction with oxygen 101 (containing argon impurity) and ethylene 102 in reactor 130 and purge stream 115 which is diverted as waste.

In an oxygen-based process argon impurities introduced with the oxygen stream determine the size of the purge stream. The amount of argon that is removed in the purge (115) equals the product of the argon concentration in the purge times the purge volume and this product must be equal to the amount of argon that is added to the reactor by the fresh oxygen feed (101) according to the equation (1) below:

$$\text{(volumetric argon concentration)} \times \text{(volumetric purge flow rate)} = \text{(volume of argon added by the fresh oxygen feed)} \quad (1)$$

If the amount of argon introduced to the process by the fresh oxygen feed decreases and argon concentration remains constant, then, according to equation (1), the size of the purge stream can be decreased and ethylene lost to the purge can be reduced. If the amount of argon introduced to the process decreases and argon concentration is reduced, then the size of the purge stream will be increased relative to the constant argon case.

EXAMPLE 1

Figure 2:
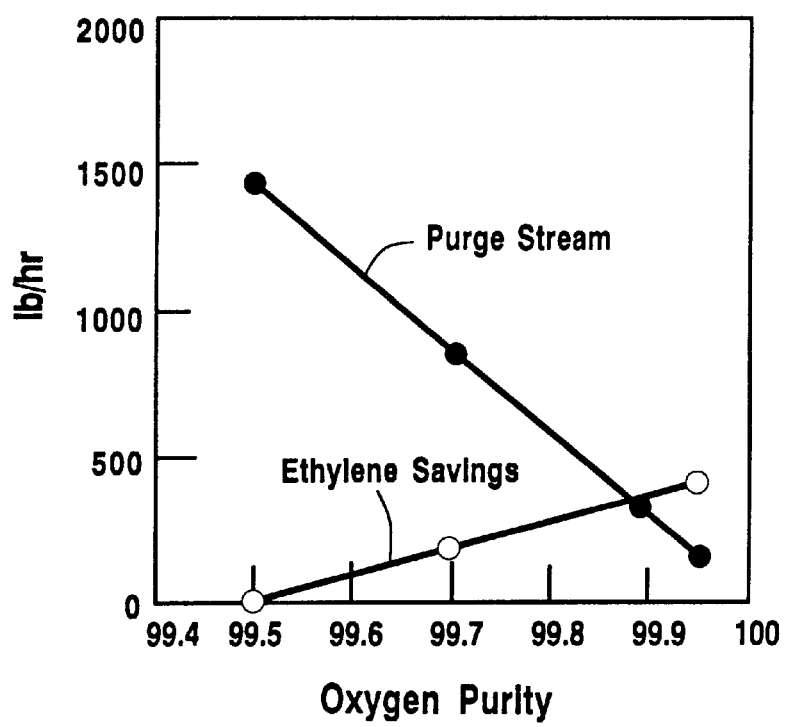
FIG. 2 is a graphical representation of the effects of the savings to ethylene and of reducing the volume of the purge stream thereby when the oxygen concentration increases from 99.5% oxygen to 99.95% oxygen, and when the argon concentration in the recycle stream is maintained at a constant 16%.

FIG. 2 provides a graphical relationship presenting the reduction of the volume of the purge stream as the oxygen purity increases. A plant producing 500 MM lb/yr ethylene oxide was used. The gas stream that is fed to the reactor tubes contains about 25 mol % ethylene, 8 mol % oxygen, 16 mol % argon, 42 mol % ballast gas methane, 6.5 mol % carbon dioxide, and the remaining as ethane and water. FIG. 2 provides that as the oxygen purity is increased from 99.5% oxygen purity to 99.95% oxygen purity, while keeping the argon concentration in the recycle stream constant at 16 mol %, the flow rate of the purge is decreased. Oxygen of purity greater than 99.5% is commercially available and referred to here as high purity oxygen. This represents the present practice of using high purity oxygen and the case in FIG. 2 is referred as the base case when it is compared with the results of this invention.

EXAMPLE 2

Figure 3:
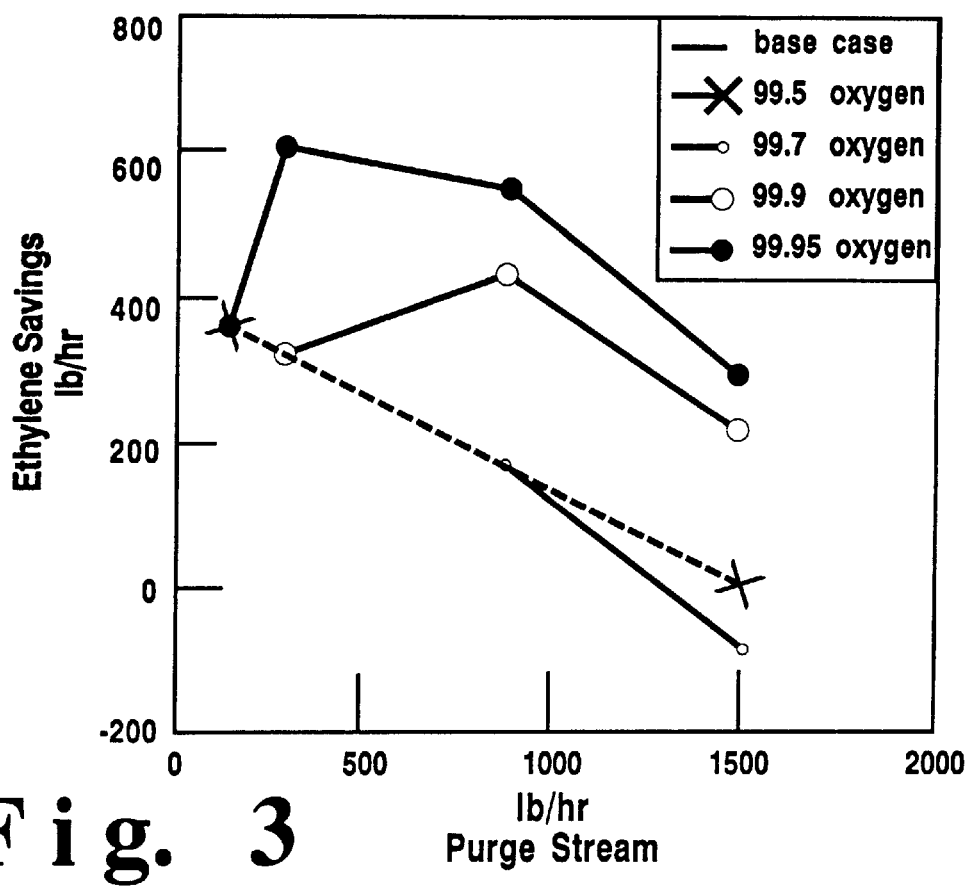
FIG. 3 is a graphical representation of the effects of the purge flow (reducing argon concentration) and the resulting ethylene savings for a variety of oxygen purity concentrations in the feed stream by assuming a selectivity improvement of 0.1% for every 1% reduction in argon concentration.

A plant producing 500 MM lb/yr ethylene oxide with an oxygen-based process is used. The gas stream that is fed to the reactor tubes contains about 25 mol % ethylene, 8 mol % oxygen, 16 mol % argon, 42 mol % ballast gas methane, 6.5 mol % carbon dioxide, and the remaining as ethane and water. The selectivity of the reaction is about 80% towards ethylene oxide. Oxygen feed with 99.5% purity represents zero ethylene savings. The concentration of argon is reduced, and its concentration is replaced by methane. The purge flow is adjusted. A selectivity improvement of 0.1% for every 1% decrease in argon concentration was used in calculating the savings. Ethylene savings were calculated as a function of the oxygen purity and the purge flow. FIG. 3 provides the results of the relationship of ethylene savings and purge stream using very high purity oxygen. It is shown in FIG. 3 that for 99.95% purity oxygen, increasing the purge flow-rate and decreasing argon concentration will initially increase the ethylene savings, but the savings will decrease as the purge flow-rate continues to increase. The maximum of the curve represents the optimum operating point and it is significantly higher than the base case savings. The maximum is achieved not only by using high purity oxygen, but also by adjusting the purge volume flow to a value that optimizes the gas concentration in the recycle stream and increases selectivity.

EXAMPLE 3

Figure 4:
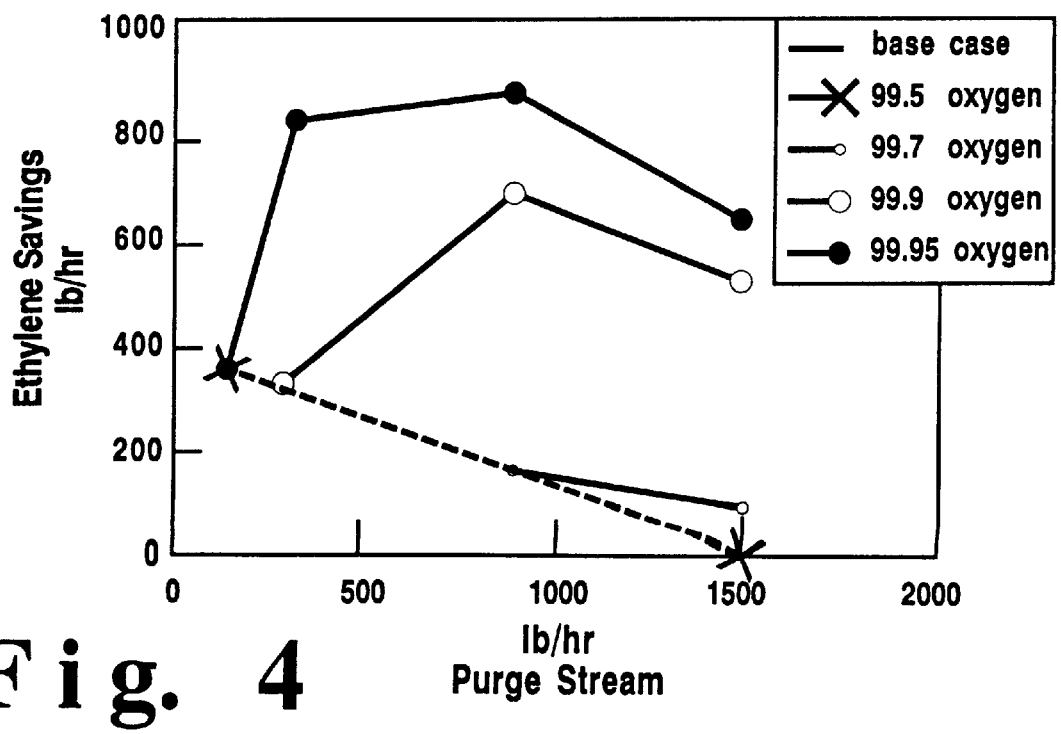
FIG. 4 is a graphical representation of the effects of the purge flow (reducing argon concentration) and the resulting ethylene savings for a variety of oxygen purity concentrations in the feed stream by assuming a selectivity improvement of 0.15% for every 1% reduction in argon concentration.

A plant producing 500 MM lb/yr ethylene oxide with an oxygen-based process is used. The gas stream that is fed to the reactor tubes contains about 25 mol % ethylene, 8 mol % oxygen, 16 mol % argon, 42 mol % ballast gas methane, 6.5 mol % carbon dioxide, and the remaining as ethane and water. The selectivity of the reaction is about 80% towards ethylene oxide. Oxygen feed with 99.5% purity represents zero ethylene savings. The concentration of argon is reduced, and its concentration is replaced by methane. The purge flow is adjusted. A selectivity improvement of 0.15% for every 1% decrease in argon concentration was used in calculating the savings. Ethylene savings may be calculated as a function of the oxygen purity and the purge flow. FIG. 4 provides the results of the relationship of ethylene savings and purge stream using high purity oxygen.

It is shown in FIG. 4 that for 99.95% purity oxygen, increasing the purge flow-rate and decreasing the argon concentration will initially increase the ethylene savings, but the savings will decrease as the purge flow-rate continues to increase. The maximum of the curve represents the optimum operating point. The maximum is achieved not only by using high purity oxygen, but also by adjusting the purge volume flow to a value that optimizes the gas concentration in the recycle stream and increases selectivity to ethylene oxide.

The present invention may also be extended to the practice of vinyl acetate monomer production and vinyl chloride production. These chemicals are produced by partial oxidation processes that use similar reactors with recycle streams and purge streams.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed is:

1. A method for enhancing the yield of ethylene oxide by reducing the presence of argon during ethylene oxide production, said method comprises a) combining ethylene, high purity gas containing at least 99.5% oxygen and a ballast gas with a recycle gas to form a gaseous reaction mixture;

b) feeding said reaction mixture into a catalyst filled reactor such that an effluent emerges therefrom;

c) passing at least a portion of said effluent from said reactor to a recovery unit to selectively remove ethylene oxide, thereby forming an ethylene oxide depleted gas stream;

d) passing at least a portion of the ethylene oxide depleted gas stream to a stripping unit to selectively remove carbon dioxide therefrom;

e) passing at least a portion of the carbon dioxide depleted gas stream to purge and the remaining portion to recycle as a recycle gas;

f) recompressing the recycle gas; and g) adjusting the flow of the purge stream to effectively reduce the concentration of argon.

2. The method of claim 1 wherein step (g) further comprises adjusting the feed flow rate of at least one of said ethylene, high purity oxygen, ballast gas, thereby increasing the selective production of said ethylene oxide.

3. The method of claim 1 wherein step (g) further comprises producing a gas with enhanced heat transport properties to reduce the effects of hot spots formed in the reactor.

4. The method of claim 3 wherein the reduction in the effects of said hot spots increases the selectivity to ethylene oxide and increases catalyst life.

5. The method of claim 1 wherein step (g) reduce the loss of ballast gas.

6. The method of claim 1 wherein said ballast gas comprises methane.

7. The method of claim 1 wherein said ballast gas comprises nitrogen.

8. The method of claim 1 wherein said catalyst filled reactor comprises a reactor tube filled with silver on a porous support.

* * * * *

(12) REEXAMINATION CERTIFICATE (4838th)
United States Patent
Papavassiliou et al.

(10) Number: US 6,040,467 C1
(45) Certificate Issued: Aug. 26, 2003

(54) HIGH PURITY OXYGEN FOR ETHYLENE OXIDE PRODUCTION

(75) Inventors: Vasilis Papavassiliou, Kent, NY (US); Matthew Lincoln Wagner, White Plains, NY (US); Roger William Day, Southbury, CT (US)

(73) Assignee: Praxair Technology, Inc., Danbury, CT (US)

Reexamination Request:
No. 90/005,926, Feb. 13, 2001

Reexamination Certificate for:
Patent No.: 6,040,467
Issued: Mar. 21, 2000
Appl. No.: 08/899,706
Filed: Jul. 24, 1997

(51) Int. Cl.$^7$ .................. C07D 301/10; C07D 301/03
(52) U.S. Cl. ............................. 549/534; 549/535
(58) Field of Search .................. 549/534, 535, 549/536, 537

(56) References Cited

U.S. PATENT DOCUMENTS 3,725,307 A * 4/1973 Brown et al. ............... 502/347
4,833,261 A * 5/1989 Lauritzen .................. 549/536
5,233,060 A   8/1993 Pendergast et al. ......... 549/523
5,519,152 A * 5/1996 Gorcester .................. 549/534

FOREIGN PATENT DOCUMENTS

| EP | 0200518 | * 11/1986 |
| GB | 1088730 | 10/1967 |
| GB | 1382099 | 1/1975 |

OTHER PUBLICATIONS

European Search Report for European counterpart to the application for the '467 patent. Dated Oct. 13, 1998.

* cited by examiner

*Primary Examiner*—D. Margaret Seaman

(57) ABSTRACT

This invention is directed to a method for producing ethylene oxide comprising feeding ethylene, high purity oxygen and a ballast gas with a recycle gas in a catalyst filled reactor to form a gaseous mixture; passing the gaseous mixture from the reactor to a recovery unit to selectively separate ethylene oxide and carbon dioxide containing gas; passing at least a portion of the carbon dioxide containing gas to a stripping unit to selectively separate carbon dioxide and a waste gas; passing at least a portion of the waste gas to purge and another portion for recycling as the recycle gas; and recovering ethylene oxide from the recovery unit.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

\* \* \* \* \*